US009308401B2

(12) United States Patent
Asada et al.

(10) Patent No.: US 9,308,401 B2
(45) Date of Patent: Apr. 12, 2016

(54) PORTABLE INTAKE AIR STERILIZING APPARATUS

(71) Applicant: TAIKO PHARMACEUTICAL CO., LTD., Suita-shi (JP)

(72) Inventors: Shigeo Asada, Ibaraki (JP); Takashi Shibata, Suita (JP)

(73) Assignee: TAIKO PHARMACEUTICAL CO., LTD., Suita-Shi, Osaka (JP)

( * ) Notice: Subject to any disclaimer, the term of this patent is extended or adjusted under 35 U.S.C. 154(b) by 0 days.

(21) Appl. No.: 14/445,150

(22) Filed: Jul. 29, 2014

(65) Prior Publication Data

US 2014/0332004 A1    Nov. 13, 2014

Related U.S. Application Data

(62) Division of application No. 12/738,058, filed as application No. PCT/JP2008/067917 on Oct. 2, 2008, now Pat. No. 9,022,035.

(30) Foreign Application Priority Data

Oct. 15, 2007    (JP) .................................. 2007-267965

(51) Int. Cl.
*A62B 23/02* (2006.01)
*A62B 23/00* (2006.01)
(Continued)

(52) U.S. Cl.
CPC . *A62B 23/02* (2013.01); *A62B 7/10* (2013.01); *A62B 11/00* (2013.01); *A62B 18/00* (2013.01);
(Continued)

(58) Field of Classification Search
CPC .......... A61M 16/0087; A61M 16/009; A61M 16/0093; A61M 16/10; A61M 16/105; A61M 16/1055; A61M 16/106; A61M 16/107; A61M 16/22; A61M 2205/75; A61M 2205/7509; A61M 2205/7518; A62B 7/10; A62B 7/08; A62B 11/00; A62B 18/00; A62B 19/00; A62B 23/00; A62B 23/02; A62B 23/025; A62B 21/00; C02F 1/4674; C02F 1/76; C02F 1/763; C02F 2303/02; C01B 11/02; C01B 11/023; C01B 11/024; C01B 11/025; C01B 11/026
USPC ........................ 128/202.26; 422/28, 120, 123
See application file for complete search history.

(56) References Cited

U.S. PATENT DOCUMENTS 4,542,080 A  *  9/1985  Phillips ............... H01M 2/0232
                                                           429/118
4,573,464 A     3/1986  Yo
(Continued)

FOREIGN PATENT DOCUMENTS

CN    1056778 C    9/2000
CN    2666485 Y    12/2004
(Continued)

OTHER PUBLICATIONS

Notification of Transmittal of Copies of Translation of the International Preliminary Report on Patentability (Form PCT/IB/338), International Preliminary Report on Patentability (Form PCT/IB/373) in English and Written Opinion (Form PCT/ISA/237) in English, mailed May 20, 2010 in corresponding PCT/JP2008/067917, International Bureau of WIPO, Geneva, CH.
(Continued)

*Primary Examiner* — Steven Douglas
*Assistant Examiner* — Colin W Stuart
(74) *Attorney, Agent, or Firm* — Buchanan Ingersoll & Rooney PC (57) ABSTRACT

A portable intake air sterilizing apparatus is disclosed, which allows prevention of a worker's infection with virus/bacteria and which can allow, at the same time, the worker to work comfortably. The apparatus includes a cover member C for covering one or both of the nose and the mouth, an air intake portion K for the inner space of the cover member C, and a chlorine dioxide slow-release portion J capable of releasing chlorine dioxide gas into an intake air in association with introduction of this intake air from the air intake portion K.

2 Claims, 6 Drawing Sheets (51) Int. Cl.
*A62B 18/00* (2006.01)
*A62B 11/00* (2006.01)
*A62B 18/02* (2006.01)
*A62B 7/10* (2006.01)
*A61L 9/014* (2006.01)
*A61L 9/015* (2006.01)
*A61L 9/04* (2006.01)
*A61L 9/12* (2006.01)

(52) U.S. Cl.
CPC ............. *A62B 18/02* (2013.01); *A62B 23/00* (2013.01); *A62B 23/025* (2013.01); *A61L 9/014* (2013.01); *A61L 9/015* (2013.01); *A61L 9/048* (2013.01); *A61L 9/12* (2013.01); *A61L 2209/14* (2013.01); *A61L 2209/15* (2013.01); *A61L 2209/22* (2013.01); *A61M 2205/75* (2013.01); *A61M 2205/7509* (2013.01); *A61M 2205/7518* (2013.01)

(56) References Cited

U.S. PATENT DOCUMENTS

| | | |
|---|---|---|
| 4,981,134 A | 1/1991 | Courtney |
| 5,086,768 A | 2/1992 | Niemeyer |
| 5,394,870 A * | 3/1995 | Johansson ............ A62B 18/006 128/201.25 |
| 6,216,693 B1 | 4/2001 | Rekow et al. |
| 6,277,178 B1 | 8/2001 | Holmquist-Brown et al. |
| 7,114,496 B1 | 10/2006 | Resnick et al. |
| 7,182,081 B2 | 2/2007 | Reisman |
| 7,213,595 B2 | 5/2007 | Capon et al. |
| 2001/0013347 A1 | 8/2001 | Rekow et al. |
| 2002/0189929 A1* | 12/2002 | Kato .................... B01D 53/007 204/157.15 |
| 2007/0044801 A1 | 3/2007 | Mathis et al. |

FOREIGN PATENT DOCUMENTS

| | | |
|---|---|---|
| JP | 60-100980 A | 6/1985 |
| JP | 10-502565 A | 3/1998 |
| JP | 2004130264 A * | 4/2004 |
| JP | 2005-87429 A | 4/2005 |
| WO | WO 96/22126 A1 | 7/1996 |

OTHER PUBLICATIONS

International Search Report (in Japanese) issued by the Japanese Patent Office on Jan. 6, 2009 as the International Searching Authority in International Application No. PCT/JP2008/067917.

* cited by examiner

PORTABLE INTAKE AIR STERILIZING APPARATUS

CROSS REFERENCE TO RELATED APPLICATION

This is a divisional of application Ser. No. 12/738,058, filed Jun. 23, 2010, which is a U.S. national phase application based on International Application No. PCT/JP2008/067917, filed on Oct. 2, 2008, which claims priority from Japanese Patent Application No. 2007-267965, filed Oct. 15, 2007, the entire content of each of which is incorporated herein by reference.

TECHNICAL FIELD

The present invention relates to a portable intake air sterilizing apparatus for use in sterilizing intake air.

BACKGROUND ART

For instance, when a worker carries out a work in an environment with virus, bacteria, or the like being afloat therein, it is necessary to prevent the worker from being infected with the virus, the bacteria, or the like. As some examples of the case when a worker carries out a work in an environment with virus, bacteria, or the like being afloat therein, such cases are conceivable where a medical personnel, a rescue worker, an epidemic researcher, etc. contacts a patient infected with respiratory virus, such as influenza virus, or where a worker is to sterilize a poultry house where avian influenza has occurred.

Conventionally, for the prevention of viral/bacterial infection, there is known a construction comprising an air intake portion for introducing ambient air, a cover member for covering a worker's nose and mouth, and a flexible tube for establishing communication and connection between the air intake portion and the inner space of the cover member, wherein inside the air intake portion, there is provided a filter allowing passage therethrough of the intake air from the air intake portion, and this filter is configured to prevent passage of the virus/bacteria (such technique like this is a widely used well-known technique, not allowing citation of any specific prior-art document).

DISCLOSURE OF THE INVENTION

In the case of the above-described conventional construction, when the intake air from the air intake portion passes the filter, the virus/bacteria contained in this intake air is/are eliminated, so infection of the worker with the virus/bacteria can be prevented. However, virus, in particular, is so small (80 to 120 nm in the case of avian influenza virus) that it is necessary to make the pore diameter of the filter extremely small in order to prevent passage of such extremely small size virus, thus resulting in very high flow passage resistance against the intake air in the course of its passage through the filter. As a result, the worker would suffer breathing difficulty and the worker could not work comfortably.

The present invention has been made in view of the above-described state of the art and its principal object is to provide a portable intake air sterilizing apparatus which allows prevention of a worker's infection with virus/bacteria and which allows, at the same time, the worker to work comfortably.

According to the first characterizing feature of the portable intake air sterilizing apparatus of the present invention, the apparatus comprises a cover member for covering one or both of the nose and the mouth, an air intake portion for the inner space of the cover member, and a chlorine dioxide slow-release portion capable of releasing chlorine dioxide gas into an intake air in association with introduction of this intake air from the air intake portion.

That is, as the chlorine dioxide slow-discharge portion releases an amount of chlorine dioxide gas into the intake air, thus inactivating virus or sterilizing bacteria contained in this intake air, even if virus, bacteria, or the like present in the atmospheric air directly enters the cover member through a gap space other than the air intake portion, it is still possible to prevent the worker from being infected with the virus/bacteria. Therefore, there is no need to provide the filter that causes significant flow resistance against the intake air drawn from the air intake portion, and the breathing difficulty for the worker can be minimized, so that the worker can work comfortably.

Accordingly, there has been achieved a portable intake air sterilizing apparatus which allows prevention of a worker's infection with virus/bacteria, or the like and which allows, at the same time, the worker to work comfortably.

According to the second characterizing feature of the present invention, the cover member comprises a bowl-shaped mask body having no air permeability, and in this mask body, there is formed the air intake portion having a dust-proof filter, and the chlorine dioxide slow-release portion is placed on the inner side of the dust-proof filter.

That is, the intake air is forced to pass the air intake portion formed in the mask body and pass the chlorine dioxide slow-release portion placed on the inner side of the dust-proof filter provided in this air intake portion. Therefore, if a further filter is provided on the inner side of the dust-proof filter and the chlorine dioxide slow-release portion is formed with utilizing the space surrounded by these dust-proof filter and further filter, the construction can be formed simple.

According to the third characterizing feature of the present invention, the cover member comprises a bowl-shaped mask body having no air permeability, and in this mask body, there is formed the air intake portion having the chlorine dioxide slow-release portion, and in an inner space covered with the cover member, there are provided an ambient air introducing portion for introducing ambient air, the ambient air introducing portion being provided separately from the air intake portion, and an adjusting valve for adjusting flow amount from the ambient air introducing portion.

That is, an ambient air introducing portion for introducing ambient air is provided in the inner space covered with the cover member separately of the air intake portion and there is also provided an adjusting valve to adjust the flow amount from the ambient air introducing portion. Therefore, by increasing the flow volume from the ambient air introducing portion by adjusting the adjusting valve in case the concentration of the chlorine dioxide gas from the air intake portion is high or by decreasing the flow amount from the ambient air introducing portion by adjusting the adjusting valve in case the concentration of the chlorine dioxide gas from the air intake portion is low, therefore the concentration of chlorine dioxide gas in the inner space covered with the cover member can be maintained appropriate in an easy manner.

According to the fourth characterizing feature of the present invention, the mask body incorporates a check valve for allowing only air to be exhaled to the outside from the inner space covered with the mask body.

That is, when the air is inhaled, the chlorine dioxide slow-release portion releases chlorine dioxide gas into this inhaled air, thus preventing virus/bacteria, or the like infection of the worker; and also, when the breathed air is exhaled, since the breathed air is exhaled to the outside from the inner space covered with the cover member through the check valve to the outside, the breathed air can be exhaled easily and smoothly, in the almost total absence of flow resistance against it. In addition, as the discharge of chlorine dioxide gas into the exhaled air is prevented by the chlorine dioxide slow-release portion, the apparatus can be used continuously for a long time.

According to the fifth characterizing feature of the present invention, the cover member comprises a mask formed of one or both of a cloth or a non-woven fabric having air permeability, and the mask functions also as the air intake portion, and the chlorine dioxide slow-release portion capable of releasing chlorine dioxide gas is formed by holding a chlorine dioxide slow-release material inside the mask.

That is, the chlorine dioxide slow-release portion can be formed by holding the chlorine dioxide slow-release material capable of releasing chlorine dioxide gas inside the mask formed of one or both of a cloth or a non-woven fabric having air permeability, virus/bacteria, or the like infection of the worker can be prevented simply with the worker's wearing of the mask.

According to the sixth characterizing feature of the present invention, the air intake portion is communicated and connected to the other end of a flexible tube whose one end is communicated and connected to the cover member, and in the air intake portion, there is formed the chlorine dioxide slow-release portion comprising a chlorine dioxide generating source including a chlorine dioxide slow-release material cable of releasing chlorine dioxide gas.

That is, as the air intake portion having the chlorine dioxide slow-release portion comprising a chlorine dioxide generating source is connected and communicated with the cover member covering one or both of the nose and the mouth via a flexible tube, the air intake portion and the cover member can be placed apart from each other. Therefore, for instance, by attaching the air intake portion to the back or around the waist of the body, it becomes possible to provide the chlorine dioxide generating source with a greater amount of the chlorine dioxide slow-release material, thus allowing use for an extended period of time.

According to the seventh characterizing feature of the present invention, the chlorine dioxide generating source comprises a generating source body having a honeycomb-like or grating-like cross section formed of a plurality of cylindrical portions for allowing passage of intake air integrated together, and on the inner side of each one of the plurality of cylindrical portions in the generating source body, the chlorine dioxide slow-release material is attached.

That is, as the intake air flows from the air intake portion through the plurality of cylindrical portions, the chlorine dioxide slow-release material attached to the inner side of each one of the plurality of cylindrical portions releases an amount of chlorine dioxide gas into the intake air. Therefore, the chlorine dioxide slow-release material can be easily contacted with the intake air. At the same time, in comparison with the arrangement of intake air being forced to pass the chlorine dioxide slow-release portion, the flow resistance experienced by the intake air in the course of its passage through the plurality of cylindrical portions can be reduced, so the breathing difficulty for the worker can be minimized; hence, the worker can work even more comfortably.

According to the eighth characterizing feature of the present invention, the chlorine dioxide slow-release material comprises an adsorbent material containing an amount of chlorine dioxide gas adsorbed thereto.

That is, an adsorbent material containing an amount of chlorine dioxide gas adsorbed thereto can be easily attached to the mask. Moreover, even when the slow-releasing ability from the adsorbent material has decreased, the material can be reused by causing the material to adsorb chlorine dioxide gas again. Furthermore, due to a pressure drop caused by intake of air within the mask, the adsorbed chlorine dioxide gas can be released in an efficient manner when needed.

According to the ninth characterizing feature of the present invention, the adsorbent material comprises a substance selected from the group consisting of a gel agent made of synthetic resin, activated charcoal, zeolite, silica gel or a mixture thereof.

That is, as the adsorbent material, a generally readily available material or substance such as a gel agent made of synthetic resin, activated charcoal, zeolite, silica gel, or the like can be employed. Also, the material can be provided inexpensively.

According to the tenth characterizing feature of the present invention, the air intake portion is communicated and connected to the other end of a flexible tube whose one end is communicated and connected to the cover member, and in the air intake portion, there is formed the chlorine dioxide slow-release portion comprising an electrolysis device for generating an amount of chlorine dioxide through an electrolysis.

That is, with an activating switch operation of the electrolysis device, the chlorine dioxide gas can be easily generated and the adjustment of the generation amount and stopping of the generation can also be executed easily.

According to the eleventh characterizing feature of the present invention, the electrolysis device includes an electrolysis bath holding therein an amount of electrolysis solution containing alkaline chloride, alkaline chlorite and a pH adjustor, a pair of electrodes submerged into the electrolysis solution held in the electrolysis bath, and a power supply unit for supplying electric current to the electrodes.

That is, the electrolysis device can be composed of the simple construction of an electrolysis bath, electrodes and a power supply unit. So, the device as a whole can be made inexpensive.

According to the twelfth characterizing feature of the present invention, there is provided an aeration device for aerating the electrolysis solution held in the electrolysis bath.

That is, chlorine dioxide gas generated by electrolysis is readily dissolvable in water, so by providing an aeration device, the chlorine dioxide gas dissolved in the electrolysis solution can be purged into the air during the use of the apparatus, whereby the supplying efficiency can be enhanced.

According to the thirteenth characterizing feature of the present invention, the aeration device comprises an intake air blowing flexible tube having its one end inserted into the electrolysis solution and having its other end connected to the cover member.

That is, only by providing an intake air blowing flexible tube, the aeration device can be prepared. Moreover, with a simple manual operation, the chlorine dioxide gas dissolved in the solution can be readily taken out into the air.

According to the fourteenth characterizing feature of the present invention, the aeration device comprises an electrically driven air pump.

That is, if the aeration device comprises an electrically driven air pump, the chlorine dioxide gas dissolved in the electrolysis solution can be purged into gas again to be taken out continuously therefrom.

According to the fifteenth characterizing feature of the present invention, the chlorine dioxide slow-release portion is configured so that in association with intake of the air from the air intake portion, the concentration of the chlorine dioxide gas contained in the intake air may range from 0.001 ppm to 0.3 ppm.

That is, if the chlorine dioxide gas concentration is below 0.001 ppm, it is difficult to inactivate virus or sterilize bacteria. On the other hand, if the chlorine dioxide gas concentration exceeds 0.3 ppm, this may provide adverse effects on the human body. Therefore, by the arrangement of rendering the chlorine dioxide gas concentration to range from 0.001 ppm to 0.3 ppm, it is possible to inactivate virus or sterilize bacteria and to prevent adverse effects on the human body at the same time.

BEST MODE OF EMBODYING THE INVENTION

The First Embodiment

In the following, a portable intake air sterilizing apparatus relating to the present invention will be described.

Figure 1:
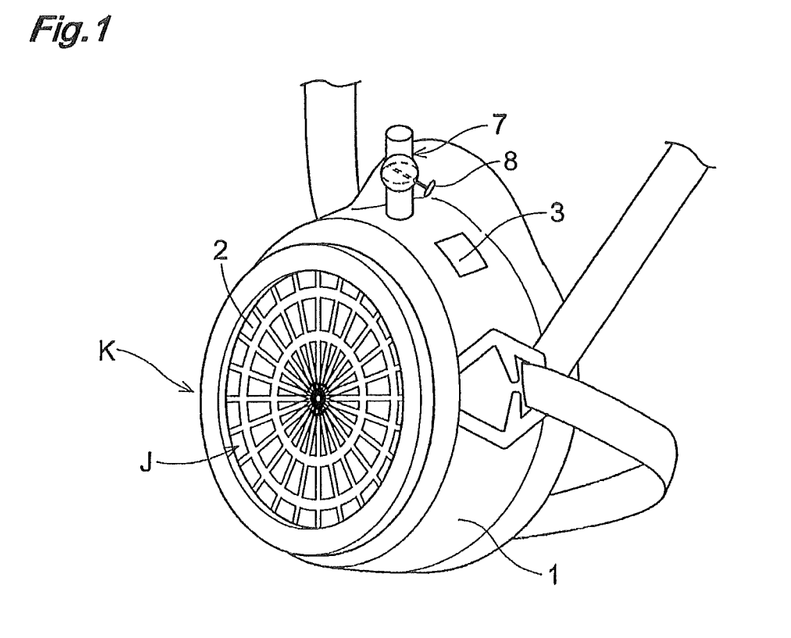
FIG. 1 is an overall perspective view of a portable intake air sterilizing apparatus relating to the first embodiment.
Figure 2:
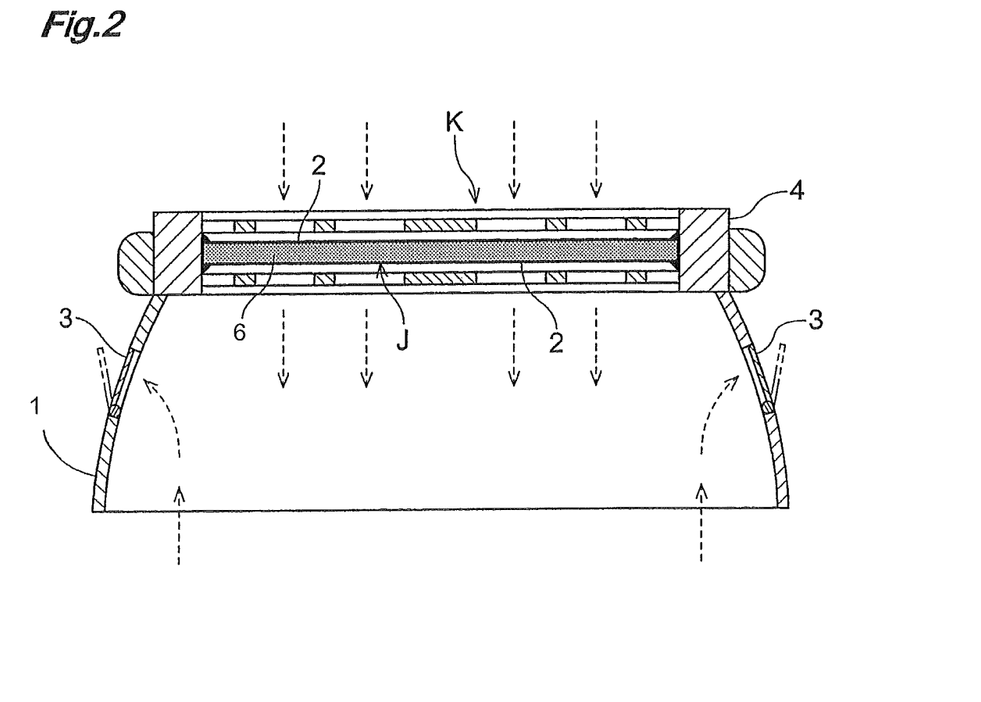
FIG. 2 is a horizontal section view of the portable intake air sterilizing apparatus relating to the first embodiment.

As shown in FIG. 1 and FIG. 2, there is provided an air-impermeable bowl-shaped mask body 1 as a cover member C for covering the nose and the mouth, and in the mask body 1, there is formed an air intake portion K having a dust-proof filter 2. And, on the inner side of this dust-proof filter 2, there is provided a chlorine dioxide slow-release portion J cable of releasing chlorine dioxide gas into intake air in association with its intake from the air intake portion K. Furthermore, in the mask body 1, there are provided check valves 3 for allowing only outlet of the air from the inner space surrounded by the mask body 1 to the outside and separately of the air intake portion K, there is also provided an ambient air inlet portion 7 for introducing ambient air to the inner space covered with the mask body 1. An ambient air valve 8 is provided as an adjusting valve for adjusting the inlet amount of the air from the ambient air introducing portion 7.

Referring more particularly to the above, at the top of the bowl-shaped mask body 1 made of resin and acting as the cover member C for covering the nose and the mouth, there is provided the substantially circular disc-shaped air intake portion K for introducing ambient air to the inner space of the mask body 1. On the front and rear sides of a lateral wall 4 of the air intake portion K, circular filter paper sheets 2 as dust-proof filters, are provided in spaced relationship with each other. And, between these circular filter paper sheets 2, there is charged an amount of particulate chlorine dioxide agent 6 as a chlorine dioxide slow-release material 5 and a gap space between the peripheral edge of each circular paper sheet 2 and the lateral wall 4, an amount of putty is filled, thus constituting a chlorine dioxide slow-release portion J altogether. On the opposing lateral sides of the air intake portion K in the mask body 1, there are provided the check valves 3 for allowing only exhaust of the air from the inner space covered with the mask body 1 to the outside, and on the upper side of the air intake portion K in the mask body 1, the cylindrical ambient air inlet portion 7 is provided. And, at a mid position of the ambient air inlet portion 7, there is provided the ambient air valve 8 as an adjusting valve for adjusting the inlet amount of the air from the ambient air introducing portion 7 by varying the air flow rate.

Referring further to the particulate chlorine dioxide agent 6, this agent was prepared by weighing 8.58 g of 80 wt % sodium hypochlorite, 25.71 g of particulate matter comprising silicate mineral salt substance (diatom earth, zeolite, kaolin, pearlite, bentonite, etc.) and 15.71 g of calcium chlorite, respectively and then mixing these together. When this was actually attached in the mask body 1 and the chlorine dioxide concentration was determined with using a chlorine dioxide gas detecting tube, a value of 0.1 ppm was detected. This concentration is between 0.001 ppm and 0.3 ppm and is capable of inactivating virus and/or sterilizing bacteria contained in the intake air and is also capable of preventing adverse effects to the human body.

The chlorine dioxide gas concentration ranges preferably from 0.01 to 0.3 ppm, more preferably from 0.1 to 0.3 ppm.

The anti-viral effect, the anti-bacterial effect, and the anti-fungal effect of chlorine dioxide can be utilized for the treatment of infectious diseases.

As examples of causative agents of viral diseases, many can be cited widely such as influenza viruses (type A, type B, and type C), avian influenza virus, coxsackievirus (causative agents of hand, foot and mouth disease, aseptic meningitis, summer cold, febrile disease, paralysis, and airway disease), AIDS virus (HIV), HHV-1 (herpes simplex virus type 1 (HSV-1)), HHV-2 (herpes simplex virus type 2 (HSV-2)), HHV-3 (chickenpox * herpes zoster virus (VZV)), HHV-5 (cytomegalovirus (CMV)), adenovirus, enterovirus, and so on.

As the causative agents of bacterial diseases, e.g. *Staphylococcus aureus, Peudomonas aeruginosa, Streptococcus, Neisseria gonorrhoea*, syphilis, and so on can be cited. Furthermore, as the causative agents of fungal diseases, *Trichophyton, Malassezia, Candida* and so on can be cited.

Furthermore, generally, for the generation of chlorine dioxide gas, an acid and water are needed. In this invention, carbon dioxide gas and water contained in the ambient air and carbon dioxide gas and water contained in the exhaled air can be utilized to this end.

The Second Embodiment

In the following, a portable intake air sterilizing apparatus will be described.

Figure 3:
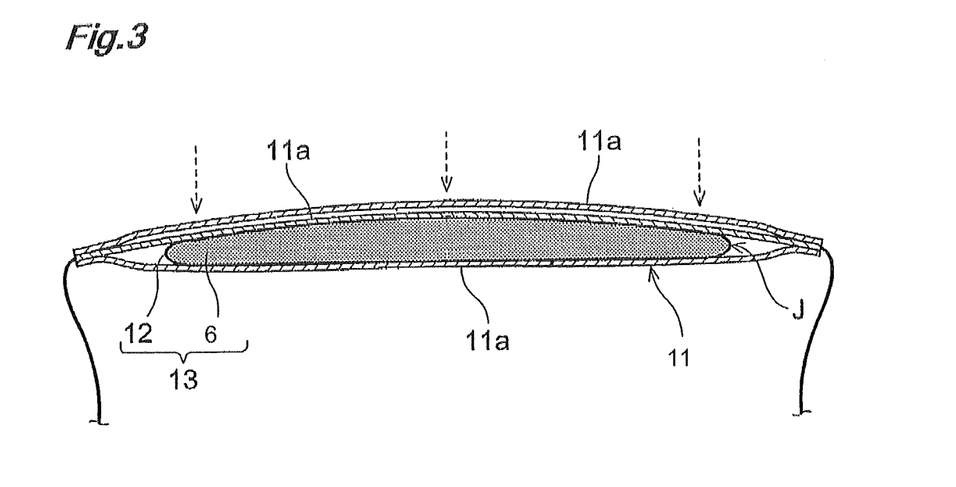
FIG. 3 is a horizontal section view of a portable intake air sterilizing apparatus relating to the second embodiment.

As shown in FIG. 3, the cover member C for covering the nose and the mouth is provided as a mask 11 formed of cloths 11a having air permeability and the chlorine dioxide slow-release material 5 is held inside the mask 11, thus constituting the chlorine dioxide slow-release portion J capable of releasing an amount of chlorine dioxide gas into the intake air in association with its intake from the mask 11.

Referring more particularly to the above, the mask 11 comprises a plurality of cloths 11a superposed in the laminar form along the thickness direction thereof, and in an air-permeable bag 12, there is charged an amount of particulate chlorine dioxide agent 6 as the chlorine dioxide slow-release material 5, thus forming a flat bag 13 and this bag 13 is inserted between these cloths 11a, thereby forming the chlorine dioxide slow-release portion J. Therefore, the mask 11 functions also as the air intake portion K.

The Third Embodiment

In the following, a portable intake air sterilizing apparatus will be described.

Figure 4:
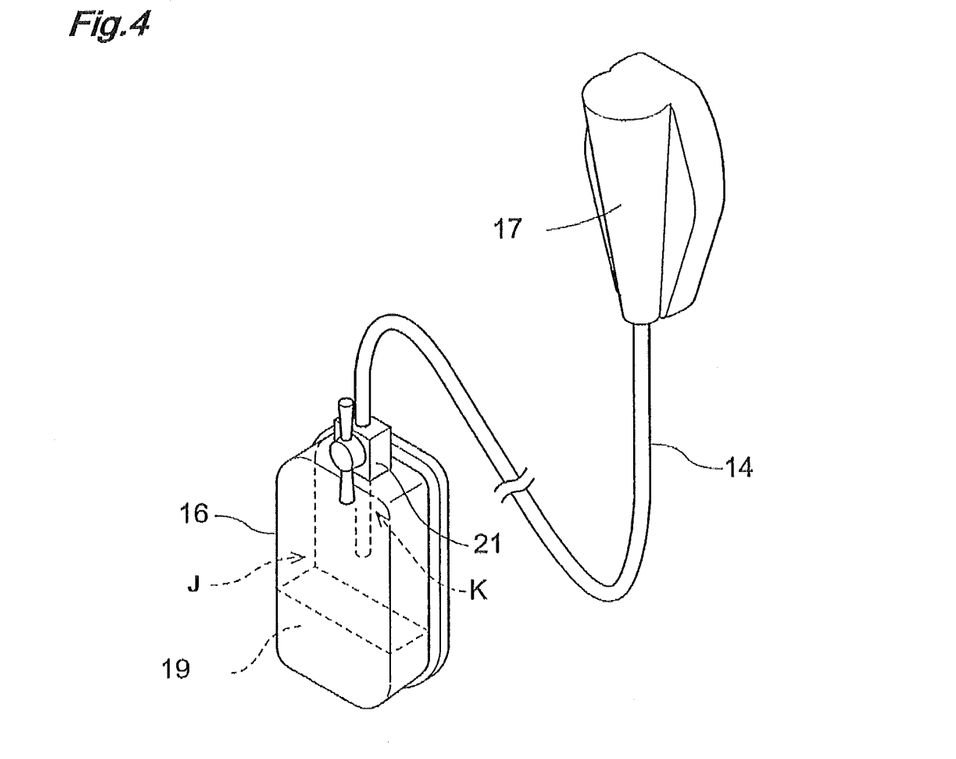
FIG. 4 is an overall perspective view of a portable intake air sterilizing apparatus relating to the third embodiment.

As shown in FIG. 4, the air intake portion K is communicated and connected to the other end of a flexible tube whose one end is communicated and connected to the cover member C, and in the air intake portion K, there is formed a chlorine dioxide slow-release portion J comprising a chlorine dioxide generating source H including a chlorine dioxide slow-release material 5 cable of releasing chlorine dioxide gas.

Referring more particularly to the above, a polyethylene container 16 having a capacity of 200 ml and an ear-hooking type cotton mask 17 having the shape preservation capability are communicated and connected to each other via a polyethylene tube 14 as a "flexible tube". Inside the polyethylene container 16, there is charged gel-like chlorine dioxide agent 19 as the chlorine dioxide slow-release material 5 to approximately one third of the container capacity, thus forming the chlorine dioxide slow-release portion J, and an air inlet (not shown) is provided in the polyethylene container 16, thus forming the air intake portion K. And, an opening/closing valve 21 is provided at the connecting portion between the polyethylene tube 14 and the polyethylene container 16.

Referring more particularly to the gel-like chlorine dioxide agent 19, for its preparation, 50 g of lithium chlorite is dissolved in 950 ml of water to prepare 50000 ppm lithium chlorite aqueous solution (Solution A). Chlorine dioxide gas is dissolved by bubbling in water to prepare 2500 ppm chlorine dioxide aqueous solution (Solution B). 10 g of lithium chlorite is dissolved in 990 ml of water to prepare 10000 ppm lithium chlorite aqueous solution and into this, 5 g of citric acid is dissolved to prepare lithium chlorite aqueous solution containing citric acid (Solution C). Thereafter, 200 ml of the lithium chlorite aqueous solution (Solution A), 700 ml of the chlorine dioxide aqueous solution (Solution B) and 100 ml of the citric acid containing, lithium chlorite aqueous solution (Solution C) are mixed and stirred sufficiently at the room temperature to prepare 1000 ml of chlorine dioxide agent (Solution D), and 384 ml of this chlorine dioxide agent (Solution D) is added to 16 g of a highly water-absorbent resin of cross-linked polyacrylate, and the resultant mixture is stirred sufficiently at the room temperature.

Then, when this was actually attached in the cotton mask 17 and the chlorine dioxide concentration was determined with using a chlorine dioxide gas detecting tube, a value of 0.1 ppm was detected. This concentration is between 0.001 ppm and 0.3 ppm and is capable of inactivating virus and/or sterilizing bacteria contained in the intake air and is also capable of preventing adverse effects to the human body.

Additionally, an electrically driven blower fan can be provided for forcibly feeding chlorine dioxide toward the cover member C inside the polyethylene tube 14.

The Fourth Embodiment

Figure 5:
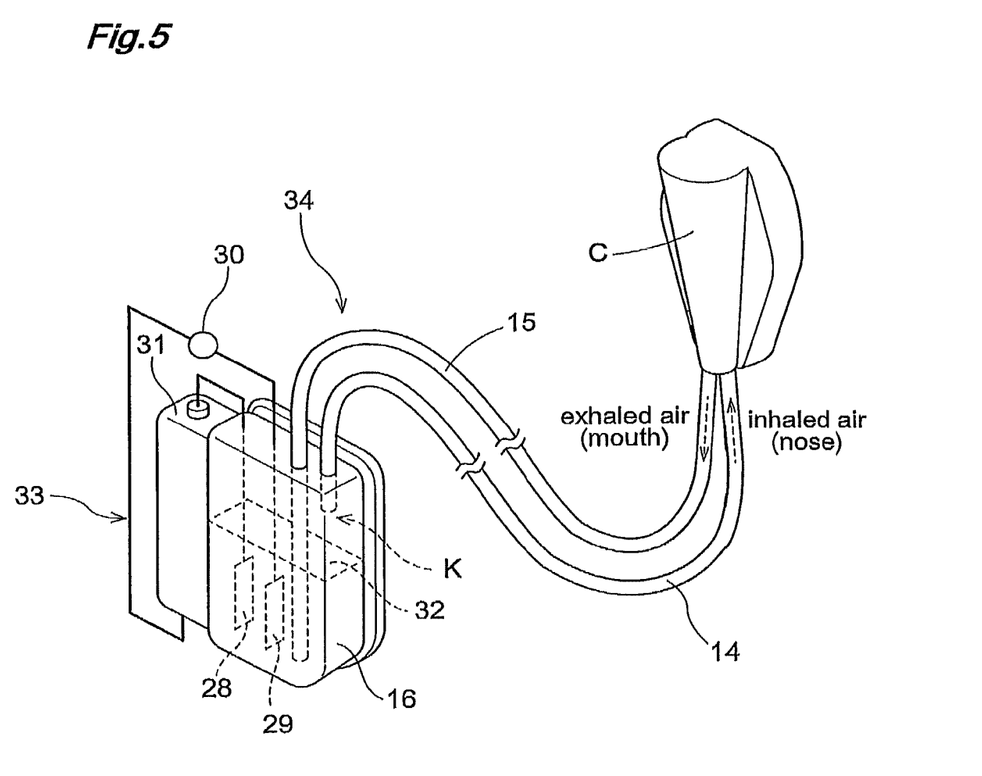
FIG. 5 is an overall perspective view of a portable intake air sterilizing apparatus relating to the fourth embodiment.

The air intake portion K is communicated and connected to the other end of a flexible tube whose one end is communicated and connected to the cover member C, and in the air intake portion K, there is provided an electrolysis device for generating an amount of chlorine dioxide gas through an electrolysis, as the chlorine dioxide slow-release portion, as shown in FIG. 5.

This electrolysis device includes an electrolysis bath (cylindrical polyethylene container 16) holding therein an amount of electrolysis solution 32 containing alkaline chloride composed of alkaline chloride, alkaline chlorite composed of sodium chlorite, and a pH adjustor composed of dibasic potassium phosphate ($K_2HPO_4$), a pair of a positive electrode 28 and a negative electrode 29 submerged into the electrolysis solution 32 held in the electrolysis bath, and a power supply unit 33 for supplying electric current to the electrodes.

The flexible tube for communicating and connecting this electrolysis device and the air intake portion is provided as a polyethylene tube 14 for introducing an amount of chlorine dioxide gas generated from the electrolysis bath to the inside of the cover member C, the positive electrode 28 is a Pt/Ir plated titanium electrode (15 mm×50 mm), and the negative electrode 29 is a titanium electrode (15 mm×50 mm).

Furthermore, the power supply unit 33 comprises a electric source such as a dry cell battery 31, the positive electrode 28, and the negative electrode 29 connected with each other via an electric current regulator 30, so as to allow adjustment of the amount of generated chlorine dioxide gas as desired through adjustment of electric current.

The electrolysis device includes an aeration device 34 for aerating the electrolysis solution 32 held in the electrolysis bath, and the aeration device 34 includes an exhaled air inlet flexible tube 15 formed of a polyethylene tube having one end thereof inserted into the electrolysis solution 32 and the other end thereof connected to the cover member C. In operation, as a user blows his/her exhaled air into the other end of the exhaled air inlet flexible tube 15 provided inside the cover member C, the inside of the electrolysis solution 32 is aerated, so that the amount of chlorine dioxide gas dissolved in the liquid can be purged out.

Figure 11:
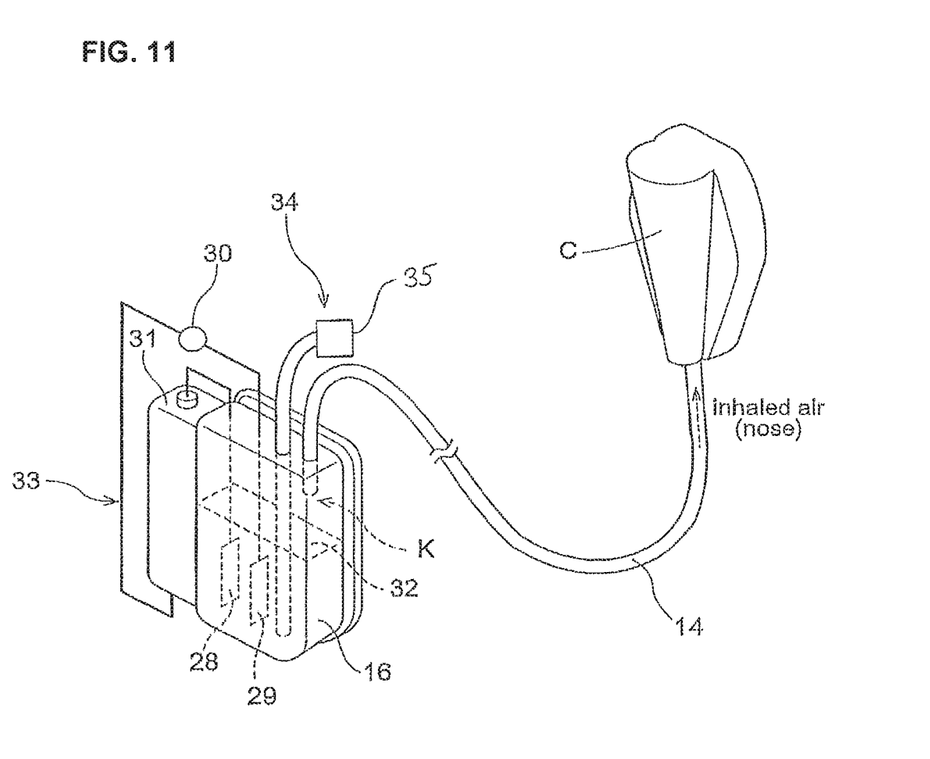
FIG. 11 is an alternative embodiment of FIG. 5.

Alternatively, as the aeration device 34, instead of providing the exhaled air inlet flexible tube 15, an electrically driven air pump 35 can be provided.

Further Embodiments (1) In the first embodiment described above, as an example of the chlorine dioxide slow-release portion J, there is described the arrangement wherein on the front and rear sides of the lateral wall 4 of the air intake portion K, the circular filter paper sheets 2 as dust-proof filters, are provided in spaced relationship with each other and between these circular filter paper sheets 2, there is charged an amount of particulate chlorine dioxide agent 6 as the chlorine dioxide slow-release material 5. Instead of this, between these circular filter paper sheets 2 and in spaced relationship relative to these circular filter paper sheets 2, an amount of gel-like chlorine dioxide agent 19 may be provided, thereby to form the chlorine dioxide slow-release portion J. Furthermore, a circular paper sheet 2 may be provided on the front side of the lateral wall 4 of the air intake portion K and an air-permeable bag 12 may be charged with particulate chlorine dioxide agent 6 as the chlorine dioxide slow-release material 5, thereby to constitute a flat shaped bag 13 and this bag 13 may be attached on the inner side of the circular paper sheet 2, thus forming the chlorine dioxide slow-release portion J. Furthermore, the chlorine dioxide slow-release portion J may be constituted by placing, on the inner side of the circular filter paper sheet 2, a communication tube connected to a small cylinder charged with a low-concentration, compressed chlorine dioxide gas therein.

(2) In the first embodiment described above, the check valves 3 were provided for allowing only exhaling the air from the inner space covered with the mask body 1 to the outside. However, the check valves 3 may not be provided.

(3) In the second embodiment described above, the cover member C was constructed as the mask 11 formed of the air-permeable cloths 11a. Instead of this construction, the cover member C can be constructed as a mask formed of air-permeable, non-woven fabric or as a mask formed of both the air-permeable cloth 11a and the non-woven fabric. That is, the mask Ills not limited to the assembly of a plurality of cloths 11a superposed in the laminar manner along the thickness direction thereof. Alternatively, the mask 11 can be constructed from a plurality of non-woven fabrics superposed in the laminated manner in the thickness direction thereof or a plurality of cloths 11a and non-woven fabrics superposed in the laminar manner along the thickness direction thereof.

Furthermore, the cover member C for covering the nose and the mouth can be a bowl-shaped mask having air-permeability and shape retentivity. In this case, on the inner side of the bowl-shaped mask, a plurality of particulate chlorine dioxide slow-release materials 5 may be distributed in the mask, or on the inner side of the bowl-shaped mask, flat shaped chlorine dioxide slow-release material 5 may be disposed in opposition to the nose and the mouth. By using such constructions, it is possible to minimize the leak of chlorine dioxide gas to the outside.

Figure 6:
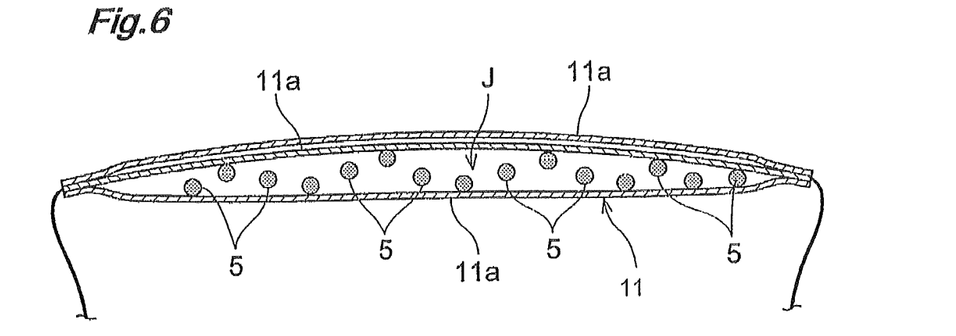
FIG. 6 is a horizontal section view of a portable intake air sterilizing apparatus relating to a further embodiment.
Figure 7:
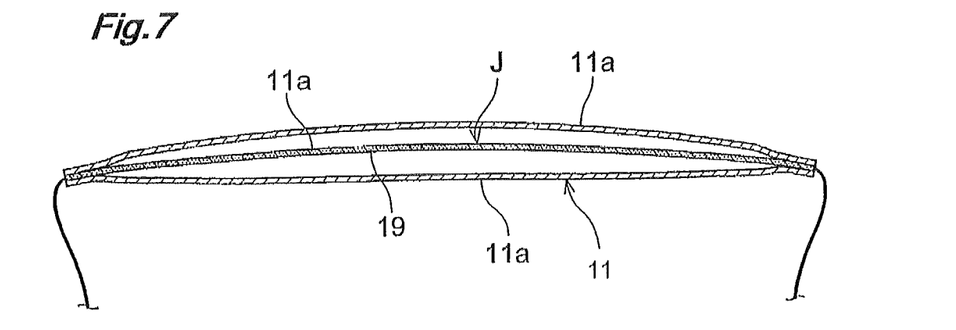
FIG. 7 is a horizontal section view of a portable intake air sterilizing apparatus relating to a further embodiment.
Figure 8:
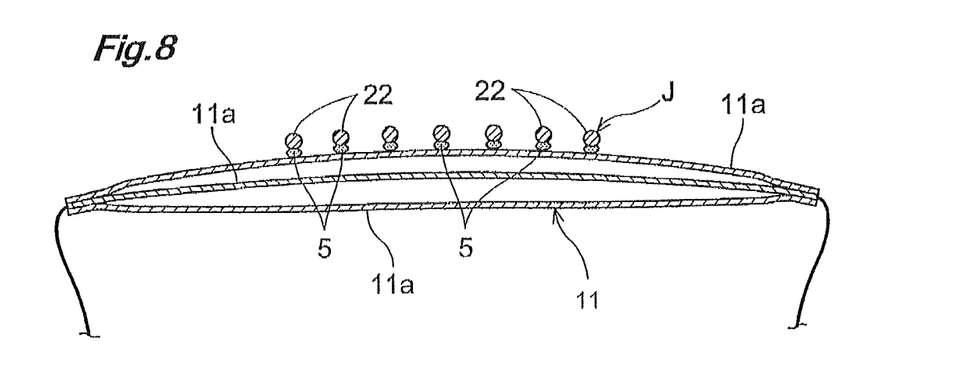
FIG. 8 is a horizontal section view of a portable intake air sterilizing apparatus relating to a further embodiment.
Figure 9:
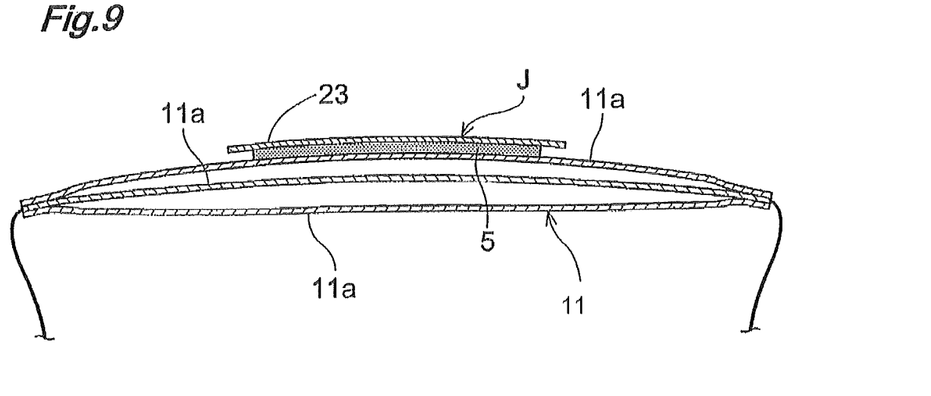
FIG. 9 is a horizontal section view of a portable intake air sterilizing apparatus relating to a further embodiment.

(4) In the second embodiment described above, there was described an exemplary arrangement in which the chlorine dioxide slow-release portion J was formed by inserting the bag 13 between the plurality of cloths 11a superposed along the thickness direction thereof. Instead of this arrangement, as shown in FIG. 6, the chlorine dioxide slow-release portion J may be formed by providing a plurality of chlorine dioxide slow-release materials 5 in distribution between the plurality of cloths 11a superposed along the direction of the thickness thereof. Furthermore, as shown in FIG. 7, the chlorine dioxide slow-release portion J may be formed by impregnating one of the plurality of cloths 11a superposed along the direction of the thickness thereof with gel-like chlorine dioxide agent 19. Still further, as shown in FIG. 8 and FIG. 9, on the outer side of the mask (the opposite side away from the nose and the mouth), a wire 22 or a plate 23 may be provided, and the chlorine dioxide slow-release material 5 may be provided on the inner side of such wire 22 or plate 23. With the use of such constructions, it is possible to minimize the leak of chlorine dioxide gas to the outside.

Figure 10:
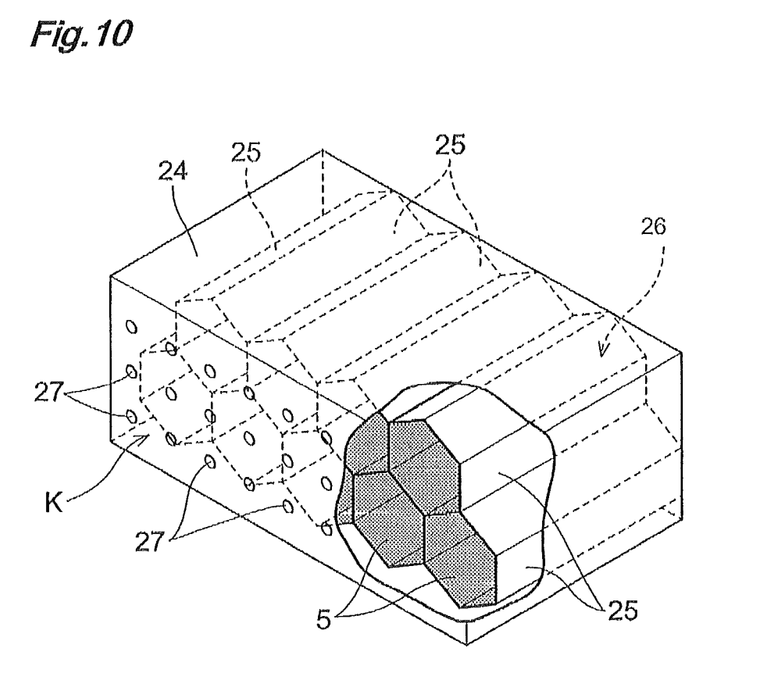
FIG. 10 is a view showing a chlorine dioxide generation source and a chlorine dioxide slow-release portion in a further embodiment.

(5) In the third embodiment described above, there was described an exemplary arrangement in which inside the polyethylene container 16, there is charged gel-like chlorine dioxide agent 19 as the chlorine dioxide slow-release material 5 to approximately one third of the container capacity, thus forming the chlorine dioxide slow-release portion J comprising the chlorine dioxide generation source H and an air intake hole (not shown) is provided in the polyethylene container 16, thus forming the air intake portion K. Instead of such arrangement, as shown in FIG. 10, inside the container 24, there may be provided a chlorine dioxide generating source H comprising a generating source body 26 having a honeycomb-like or grating-like cross section formed of a plurality of cylindrical portions 25 for allowing passage of intake air integrated together, and on the inner side of each one of the plurality of cylindrical portions 25 in the generating source body 26, the chlorine dioxide slow-release material 5 is attached. And, the air intake portion K may be formed by providing air intake holes 27 on the upstream side in the flow direction of the intake air in the container 24. Furthermore, the generating source body 26 is not limited to the one having the honeycomb-like cross section, but may have a variety of forms such as a grating-like form of triangular grating, square grating, etc.

(6) In the respective foregoing embodiments, there were explained the exemplary constructions in which the cover member C for covering the nose and the mouth is provided. Instead of such construction, there may be provided a cover member C for covering only the nose or a cover member C for covering only the mouth. As some specific examples of the cover member C for covering only the nose, there can be cited a nose mask to be inserted into the nose hole or a tube to be placed below the nose.

(7) In the first and second embodiments described above, there were explained the exemplary constructions in which the chlorine dioxide slow-release material 5 is provided as the particulate chlorine dioxide agent 6 comprising sodium hypochlorite, silicate mineral substance, and calcium chlorite. To this, a pH adjustor such as citric acid may be added.

(8) The chlorine dioxide slow-release material 5 may be an adsorbent material containing an amount of chlorine dioxide gas adsorbed thereto. This adsorbent material may be a substance selected from the group consisting of a gelling agent made of synthetic resin, activated charcoal, zeolite, silica gel or a mixture thereof.

INDUSTRIAL APPLICABILITY

The present invention is applicable to a variety of portable intake air sterilizing apparatus comprising a cover member for covering one or both of the nose and the mouth, an air intake portion for the inner space of the cover member, and a chlorine dioxide slow-release portion capable of releasing chlorine dioxide gas into an intake air in association with introduction of this intake air from the air intake portion.

What is claimed is:

1. A portable intake air sterilizing apparatus, comprising:
   a cover member for covering one or both of a nose and a mouth;
   an air intake portion for an inner space of the cover member; and
   a chlorine dioxide slow-release portion capable of releasing chlorine dioxide gas into an intake air in association with introduction of this intake air from the air intake portion, wherein
   the air intake portion is communicated and connected to an end of a flexible tube whose other end is communicated and connected to the cover member, and in the air intake portion, there is formed the chlorine dioxide slow-release portion comprising an electrolysis device for generating an amount of chlorine dioxide through an electrolysis,
   the electrolysis device includes an electrolysis bath holding therein an amount of electrolysis solution containing alkaline chloride, alkaline chlorite and a pH adjustor, a pair of electrodes submerged into the electrolysis solution held in the electrolysis bath, and a power supply unit for supplying electric current to the electrodes,
   an aeration device configured to aerate the electrolysis solution held in the electrolysis bath, and
   the aeration device comprises an intake air blowing flexible tube having its one end inserted into the electrolysis solution and having its other end connected to the cover member.

2. The portable intake air sterilizing apparatus according to claim 1, wherein the chlorine dioxide slow-release portion is configured so that in association with intake of the intake air from the air intake portion, the concentration of the chlorine dioxide gas contained in the intake air ranges from 0.001 ppm to 0.3 ppm.

* * * * *